United States Patent
Kohda

(10) Patent No.: US 6,710,365 B2
(45) Date of Patent: Mar. 23, 2004

(54) RADIATION IMAGE READ-OUT APPARATUS

(75) Inventor: Katsuhiro Kohda, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 478 days.

(21) Appl. No.: 09/863,471

(22) Filed: May 24, 2001

(65) Prior Publication Data

US 2001/0054683 A1 Dec. 27, 2001

(30) Foreign Application Priority Data

May 24, 2000 (JP) ....................................... 2000-153324

(51) Int. Cl.[7] ............................................. G01N 23/04
(52) U.S. Cl. ...................................... 250/586; 250/585
(58) Field of Search ................................. 250/584–586

(56) References Cited

U.S. PATENT DOCUMENTS

| | | | |
|---|---|---|---|
| 4,816,679 A | 3/1989 | Sunagawa et al. | 250/327.2 |
| 4,922,103 A | 5/1990 | Kawajiri et al. | 250/327.2 |
| 6,444,997 B2 * | 9/2002 | Isoda | 250/587 |

FOREIGN PATENT DOCUMENTS

| | | | |
|---|---|---|---|
| JP | 60-111568 | 6/1985 | ............ H04N/1/04 |
| JP | 60-236354 | 11/1985 | ............ H04N/1/04 |
| JP | 1-101540 | 4/1989 | ............ G03B/42/02 |

OTHER PUBLICATIONS

English language Abstract. JP 1101540. Apr. 19, 1989.

* cited by examiner

*Primary Examiner*—Zander V. Smith
(74) *Attorney, Agent, or Firm*—Sughrue Mion, PLLC

(57) ABSTRACT

In a radiation image read-out apparatus, a line stimulating light beam is projected onto a stimulable phosphor sheet, and stimulated emission emitted from the irradiated portion of the stimulable phosphor sheet is detected by a line sensor. A refractive index profile type lens array is disposed between the stimulable phosphor sheet and the line sensor. The photoelectric convertor elements of the line sensor and the refractive index profile type lenses of the refractive index profile type lens array are arranged at pitches such that the frequency band of the periodic pattern generated due to the pitches of the refractive index profile type lenses in said refractive index profile type lens array are higher than the frequency band of a radiation image information reproduced on the basis of the image signal.

5 Claims, 10 Drawing Sheets

F I G. 4
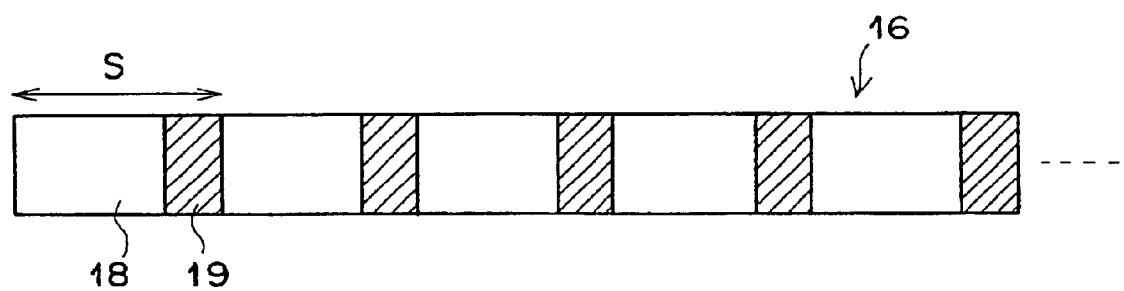

F I G . 7
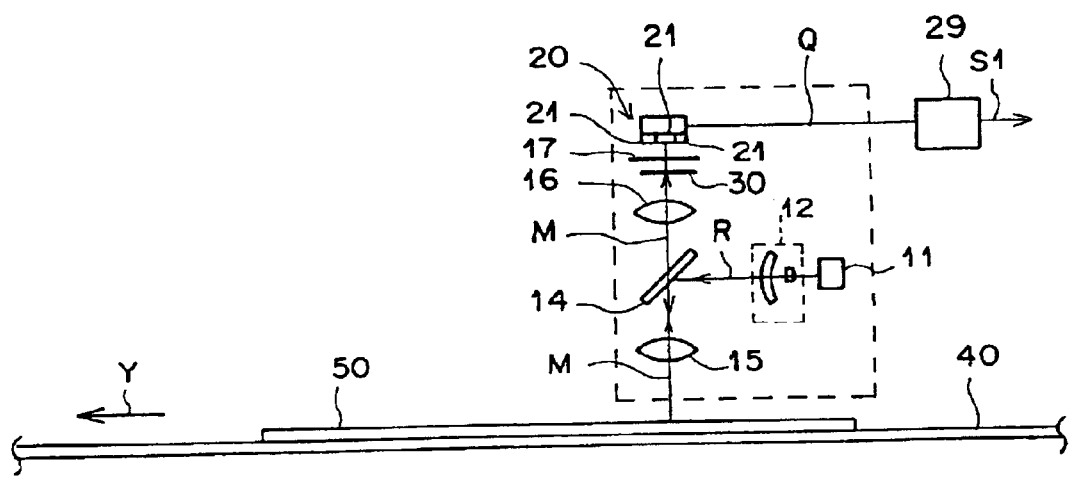

RADIATION IMAGE READ-OUT APPARATUS

BACKGROUND OF THE INVENTION

1. Field of the Invention

This invention relates to a radiation image read-out apparatus, and more particularly to a radiation image read-out apparatus for reading out a radiation image stored on a stimulable phosphor sheet by the use of a line sensor.

2. Description of the Related Art

When certain kinds of phosphor are exposed to a radiation, they store a part of energy of the radiation. Then when the phosphor which has been exposed to the radiation is exposed to stimulating rays such as visible light or a laser beam, light is emitted from the phosphor in proportion to the stored energy of the radiation. A phosphor exhibiting such properties is generally referred to as "a stimulable phosphor". In this specification, the light emitted from the stimulable phosphor upon stimulation thereof will be referred to as "stimulated emission". There has been known a radiation image read-out apparatus in which a stimulating light beam such as a laser beam is caused to scan a stimulable phosphor sheet (a sheet provided with a layer of the stimulable phosphor) which has been exposed to a radiation passing through an object such as a human body to have a radiation image of the object stored on the stimulable phosphor sheet, the stimulated emission emitted from the stimulable phosphor sheet pixel by pixel is photoelectrically detected, thereby obtaining an image signal (a radiation image signal), and then the stimulable phosphor sheet is exposed to erasing light after the image signal is obtained from the stimulable phosphor sheet so that the residual energy of the radiation is fully released from the stimulable phosphor sheet.

The radiation image signal thus obtained is subjected to image processing such as gradation processing and/or frequency processing and a radiation image of the object is reproduced as a visible image for diagnosis on the basis of the processed radiation image signal on a recording medium such as a photographic film or a display such as a fine CRT. When the stimulable phosphor sheet is exposed to erasing light, the residual energy of the radiation is fully released from the stimulable phosphor sheet and the stimulable phosphor sheet comes to be able to store a radiation image again, whereby the stimulable phosphor sheet can be repeatedly used.

In the radiation image read-out apparatus, it has been proposed to use a line light source which projects a line beam onto the stimulable phosphor sheet as a stimulating light source and to use a line sensor having an array of photoelectric convertor elements as a means for photoelectrically reading out the stimulated emission. The line beam is moved relative to the stimulable phosphor sheet and the line sensor in the direction perpendicular to the longitudinal direction of the line beam by a scanning means. By the use of a line beam and a line sensor, the reading time is shortened, the overall size of the apparatus can be reduced and the cost can be reduced. See, for instance, Japanese Unexamined Patent Publication Nos. 60(1985)-111568, 60(1985)-236354, and 1(1989)-101540.

In the conventional radiation image read-out apparatus using such a line sensor, there has been proposed a system in which is employed a refractive index profile type lens array such as a SELFOC® lens array, a rod lens array or the like, which is formed by an imaging system where the object plane and the image plane are in one to one correspondence, in order to increase convergence of the stimulated emission on the line sensor. The refractive index profile type lens array comprises a plurality of refractive index profile type lenses which are arranged according to the arrangement of the photoelectric convertor elements in the line sensor.

For example, when the photoelectric convertor elements are arranged as shown in FIG. 2 in the line sensor, the refractive index profile type lenses in the refractive index profile type lens array are arranged as shown in FIG. 3.

Use of such a refractive index profile type lens array has involved the following problem. That is, in the refractive index profile type lens array, there are formed non-aperture portions, where no lens exists, between lenses. The convergence of the stimulated emission is naturally lower in areas corresponding to the non-aperture portions, which results in a periodic pattern like stripes which extend in the direction perpendicular to the longitudinal direction of the line sensor and appear in a reproduced image at the pitches of the non-aperture portions.

SUMMARY OF THE INVENTION

In view of the foregoing observations and description, the primary object of the present invention is to provide a radiation image read-out apparatus in which the periodic pattern like stripes due to the non-aperture portions in the refractive index profile type lens array is suppressed.

In accordance with the present invention, there is provided a radiation image read-out apparatus comprising a line stimulating light beam source which projects a line stimulating light beam onto a stimulable phosphor sheet storing thereon radiation image information, a line sensor which comprises a plurality of photoelectric convertor elements arranged in the longitudinal direction of the line irradiated portion to receive stimulated emission emitted from the irradiated portion of the stimulable phosphor sheet or the back side of the sheet opposed to the line irradiated portion and convert the amount of stimulated emission to an electric signal, a light collector means which is disposed between the stimulable phosphor sheet and the line sensor and includes a refractive index profile type lens array which converges the stimulated emission onto the respective photoelectric convertor elements of the line sensor, a scanning means which moves the stimulating light beam source and the line sensor relatively to the stimulable phosphor sheet in a direction different form said longitudinal direction, and an image signal read-out means which reads out the output of the line sensor in sequence in the respective positions in which the stimulating light beam and the line sensor are moved by the scanning means and reads out an image signal representing the radiation image information stored in the stimulable phosphor sheet, wherein the improvement comprises that the photoelectric convertor elements of the line sensor and the refractive index profile type lenses of the refractive index profile type lens array are arranged at pitches such that the frequency band of the periodic pattern generated due to the pitches of the refractive index profile type lenses in said refractive index profile type lens array are higher than the frequency band of a radiation image information reproduced on the basis of the image signal.

The frequency band of a radiation image information reproduced on the basis of the image signal varies by the kind of the radiation image. In the case of a normal radiation image, the frequency band is 3 to 5 cycle/mm and in the case of a radiation image where a high sharpness is required, the frequency band is 5 to 10 cycle/mm. In this invention, the pitches of the photoelectric convertor elements of the line sensor and the refractive index profile type lenses of the refractive index profile type lens array are set to be higher than the frequency band.

As the line stimulating light beam source, a fluorescent lamp, a cold cathode tube, an LED array and the like can be employed. The line stimulating light beam source itself need not be linear so long as the stimulating light is projected onto the stimulable phosphor sheet in the form of a line beam. That is, the line stimulating light beam source may be provided with an optical system which shapes light emitted from the light source into a line beam. Further, a broad area laser may be employed as the linear stimulating light beam source. The stimulating light beam may be continuously emitted from the light beam source or may be emitted therefrom in a pulse-like fashion. From the viewpoint of reduction in noise, preferably the line stimulating light beam is in the form of high output pulsed light.

It is preferred that the length of the line stimulating light beam on the stimulable phosphor sheet (or the irradiated area of the stimulable phosphor sheet irradiated by the line stimulating light beam) be equivalent to or larger than the length of the side of the stimulable phosphor sheet. In this case, the line stimulating light beam may be projected obliquely to the side of the stimulable phosphor sheet.

In order to increase the degree of convergence of the stimulating light beam on the surface of the stimulable phosphor sheet, an optical system comprising a cylindrical lens, a slit, a SELFOC lens array, an optical fiber bundle, or a combination of these elements may be provided between the stimulating light beam source and the stimulable phosphor sheet. When an optimal second stimulating wavelength of the stimulable phosphor sheet is 600 nm or so, it is preferred that the phosphor be activated with $Eu^{3+}$ (luminescent center) and the stimulable phosphor layer be supported on a support sheet of glass or high polymer.

The width of the stimulating light beam on the surface of the stimulable phosphor sheet is preferably 10 to 4000 $\mu$m.

As the line sensor, an amorphous silicon sensor, a CCD sensor, a CCD with back illuminator, a MOS image sensor or the like may be used.

The refractive index profile type lens array of the light collector means generally comprises a SELFOC® lens array or rod lens array which is formed by an imaging system where the object plane and the image plane are in one to one correspondence in order to collect the stimulated emission emitted from respective parts of the stimulable phosphor sheet, and is generally formed of glass or high polymer material.

It is further preferred the light collector means is provided, in addition to the refractive index profile type lens array, with at least one of a cylindrical lens, a slit, an optical fiber bundle and the like.

It is further preferred that a stimulating light cut filter (a sharp cut filter, a band pass filter and such) which does not transmit the stimulating light but transmits the stimulated emission be provided between the stimulable phosphor sheet and the line sensor to prevent the stimulating light from entering the line sensor.

The light receiving face of each of the photoelectric convertor elements of the line sensor is set to be smaller than the width of the stimulated emission as seen on the light receiving face of the line sensor for the width of the irradiated area described above, and a plurality of photoelectric convertor elements are arranged in the longitudinal direction of the stimulated emission so that the overall line sensor is equal to or larger than the stimulated emission in length.

The line sensor may be provided with a plurality of photoelectric convertor elements also in the direction perpendicular to the longitudinal direction of the line stimulating light beam projected onto the stimulable phosphor sheet. In this case, the photoelectric convertor elements need not be arranged in a straight line in each of the longitudinal and transverse directions of the line sensor but may be arranged in other patterns. For example, the photoelectric convertor elements may be arranged zigzag in the transverse direction of the stimulated emission and arranged in a straight line in the longitudinal direction, and may be arranged zigzag in the longitudinal direction of the stimulated emission and arranged in a straight line in the transverse direction. Further, the photoelectric convertor elements may be arranged zigzag in both the longitudinal direction and the transverse direction.

When the number of photoelectric convertor elements is large to such an extent that influence of transfer rate is recognizable, shortening of charge accumulating time due to increase in charge transfer time may be avoided by once storing the charge accumulated in each photoelectric convertor element in a memory, and reading out the charge from the memory during a next charge accumulating cycle.

It is preferred that the line sensor includes not less than 1000 photoelectric convertor elements in the longitudinal direction thereof, and that the light receiving face of the line sensor be not shorter than the corresponding side of the stimulable phosphor sheet.

The direction in which the scanning means moves the line stimulating light beam source and the line sensor relatively to the stimulable phosphor sheet is preferably a direction substantially perpendicular to the longitudinal direction of the line stimulating light beam source and the line sensor but maybe any direction so long as substantially the entire surface of the stimulable phosphor sheet can be uniformly exposed to the stimulating light beam. For example, when the line stimulating light beam source and the line sensor are longer than the side of the stimulable phosphor sheet, the scanning means may move obliquely or zigzag the line stimulating beam source and the line sensor relatively to the stimulable phosphor sheet.

The line sensor may receive stimulated emission from the same side of the stimulable phosphor sheet as the side onto which the stimulating light beam is projected or from the back side of the stimulable phosphor sheet opposite to the side onto which the stimulating light beam is projected. In the latter case, the support sheet on which the stimulable phosphor layer is supported should be permeable to the stimulated emission.

When the photoelectric convertor elements of the line sensor and the refractive index profile type lenses of the refractive index profile type lens array are arranged at pitches such that the frequency band of the periodic pattern generated due to the pitches of the refractive index profile type lenses in said refractive index profile type lens array are higher than the frequency band of a radiation image information reproduced on the basis of the image signal as in the present invention, the periodic pattern is included in the image signal as aliasing noise. Accordingly, it is preferred that the radiation image read-out apparatus of this invention be further provided with a frequency component removal means which removes a frequency component corresponding to the frequency band of the periodic pattern from the image signal.

The frequency component removal means may comprise an optical low-pass filter disposed upstream of the line sensor, or an electric low-pass filter or digital filter which removes aliasing noise from the image signal.

It is further preferred that the pitch S of the refractive index profile type lenses be not larger than double the pitch L of the photoelectric convertor elements of the line sensor ($S \leq 2L$).

Further, it is preferred that the pitch L of the photoelectric convertor elements of the line sensor be in the range of 25 µm to 250 µm. Though it is preferred that the pitch S of the refractive index profile type lenses be as small as possible, the pitch S of the refractive index profile type lenses is preferably in the range of 10 µm to 500 µm from the viewpoint of easiness of manufacture.

In accordance with the present invention, since the photoelectric convertor elements of the line sensor and the refractive index profile type lenses of the refractive index profile type lens array are arranged at pitches such that the frequency band of the periodic pattern generated due to the pitches of the refractive index profile type lenses in said refractive index profile type lens array are higher than the frequency band of a radiation image information reproduced on the basis of the image signal, unevenness due to the non-aperture portions of the refractive index profile type lens array is not included in the image signal, whereby a sharp image free from stripe-like unevenness due to the non-aperture portions of the refractive index profile type lens array can be obtained.

Further, by removing a frequency component corresponding to the frequency band of the periodic pattern from the image signal, a sharper image free from aliasing noise can be obtained.

BRIEF DESCRIPTION OF THE DRAWINGS

FIG. 4 is a fragmentary cross-sectional view showing in detail the second SELFOC lens array, FIG. 7 is a view similar to FIG. 1B but showing a modification of the radiation image read-out apparatus shown in FIG. 1A.

DESCRIPTION OF THE PREFERRED EMBODIMENT

Figure 1A:
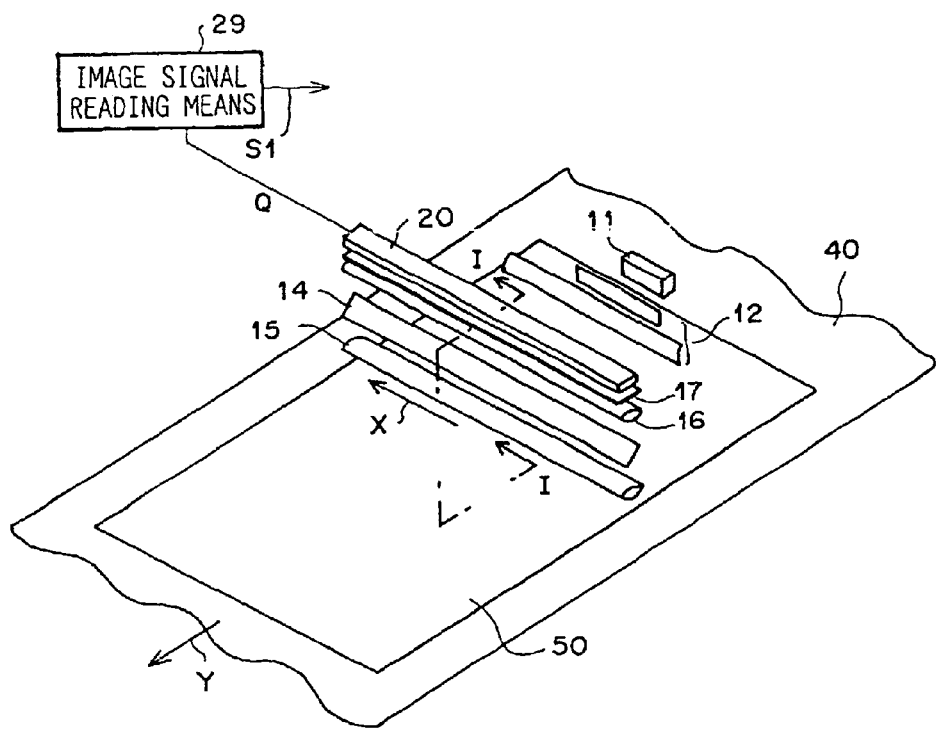
FIG. 1A is a schematic perspective view of a radiation image read-out apparatus in accordance with an embodiment of the present invention.
Figure 1B:
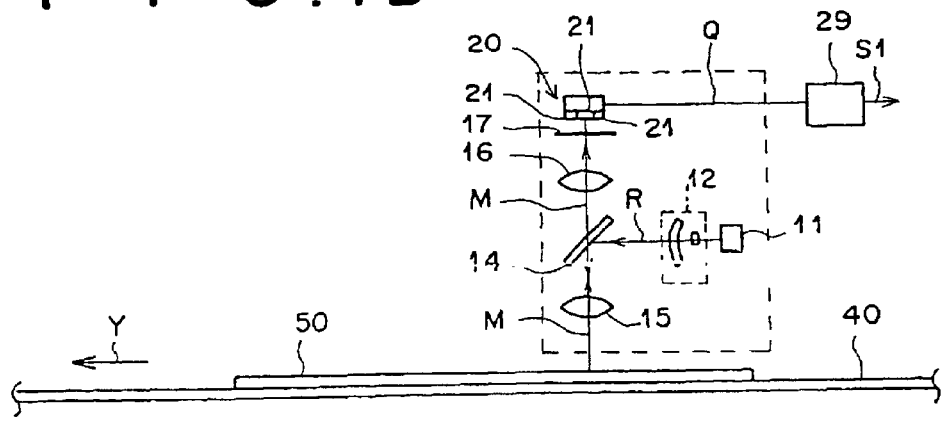
FIG. 1B is a schematic cross-sectional view taken along line I—I in FIG. 1A.

In FIGS. 1A and 1B, a radiation image read-out apparatus in accordance with a first embodiment of the present invention comprises an endless belt (a scanning means) 40 which conveys a stimulable phosphor sheet 50 (storing thereon a radiation image) in the direction of arrow Y; a broad area laser 11 which emits a line (secondary) stimulating light beam R substantially 100 µm wide in parallel to the surface of the stimulable phosphor sheet 50; an optical system 12 formed by a combination of a collimator lens which condenses the line stimulating light beam R emitted from the broad area laser 11 and a toric lens which spreads the light beam only in one direction; a dichroic mirror 14 which is inclined at 45° to the surface of the stimulable phosphor sheet 50 and transmits stimulated emission M while reflecting the line stimulating light beam R; a first SELFOC lens array 15 which is an array of a plurality of refractive index profile type lenses, converges the line stimulating light beam R reflected by the dichroic mirror 14 to impinge upon the stimulable phosphor sheet 50 in a pattern of a line about 100 µm wide extending in the direction of arrow X and collimates into a parallel light bundle stimulated emission M emitted from the part of the stimulable phosphor sheet 50 exposed to the line stimulating light beam R; a second SELFOC lens array 16 which converges the stimulated emission M which passes through the dichroic mirror 14 onto the light receiving face of a line sensor 20; a stimulating light cut filter 17 which cuts the stimulating light L in the stimulated emission M passing through the second SELFOC lens array 16; the line sensor 20 which has an array of photoelectric convertor elements 21 which receive the stimulated emission M and convert it into an electric signal Q; and an image signal reading means 29 which reads the electric signals Q output from the respective photoelectric convertor elements 21 in sequence as the stimulable phosphor sheet 50 is moved and outputs an image signal S1 representing a radiation image stored on the stimulable phosphor sheet 50.

The optical system 12 formed by the collimator lens and the toric lens enlarges the image of the line stimulating light beam R from the broad area laser 11 to a desired size, thereby changing the irradiation size.

Figure 2:
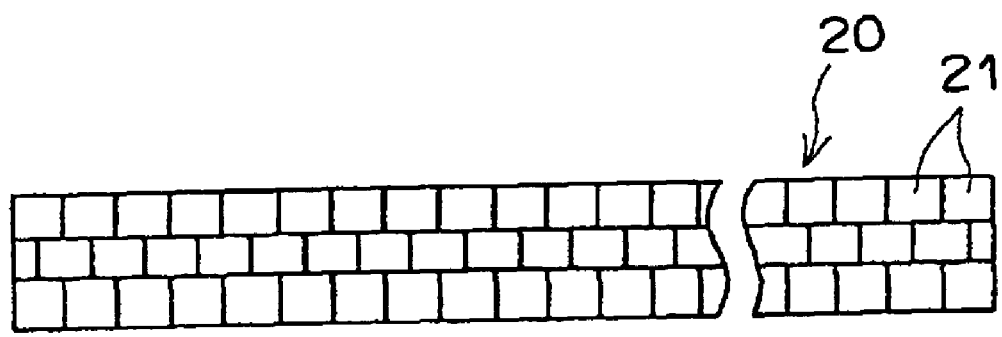
FIG. 2 is a view showing in detail the line sensor employed in the radiation image read-out apparatus shown in FIGS. 1A and 1B.

As shown in FIG. 2, the line sensor 20 comprises three photoelectric convertor element arrays. Each photoelectric convertor element array comprises a number of (e.g., 1000 or more) photoelectric convertor elements 21 arranged in the direction of arrow X. The three arrays are arranged zigzag in the direction of conveyance of the stimulable phosphor sheet 50 (the direction of arrow Y). The photoelectric convertor element 21 may be, for instance, an amorphous silicon sensor, a CCD sensor or a MOS image sensor.

Figure shows the arrangement of the first and second SELFOC lens arrays 15 and 16. As can be understood from FIG. 3, in the first and second SELFOC lens arrays 15 and 16, a plurality of refractive index profile type lenses 18 are arranged to correspond to the photoelectric convertor elements 21 of the line sensor 20. The first SELFOC lens array 15 images a light emitting region of the stimulable phosphor sheet 50 on the dichroic mirror 14 in a natural size, and the second SELFOC lens array 16 transfers the image of the light emitting region of the stimulable phosphor sheet 50 on the dichroic mirror 14 to the light receiving face of the line sensor 20 in a natural size.

Figure 3:
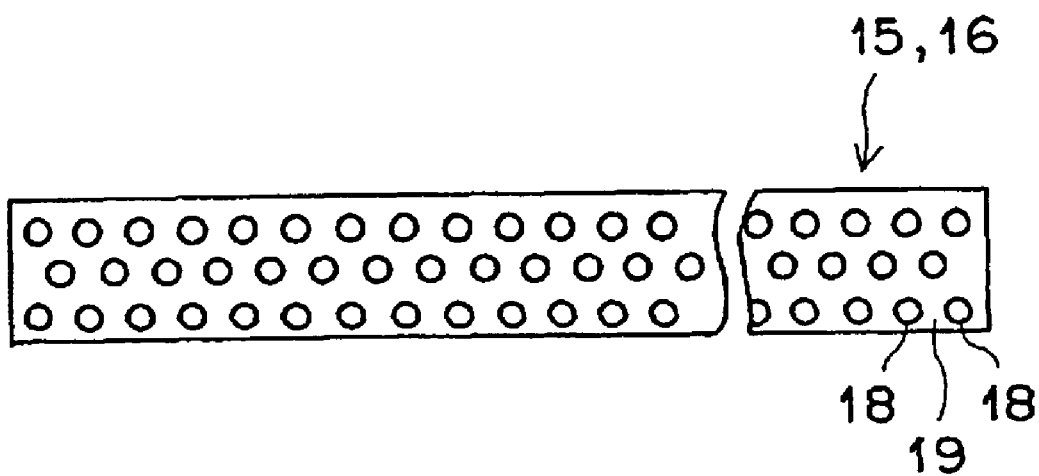
FIG. 3 is a cross-sectional view showing in detail the first and second SELFOC lens arrays.

As shown in FIG. 3, a non-aperture portion 19 is formed between refractive index profile type lenses 18 and the non-aperture portions 19 are arranged to form an array. The stimulated emission M emitted from the stimulable phosphor sheet 50 impinges upon the photoelectric convertor elements 21 passing through not only the refractive index profile type lenses 18 but also the non-aperture portions 19.

The convergence of the stimulated emission M is naturally lower in areas corresponding to the non-aperture portions 19, which results in a periodic pattern like stripes which extend in the direction perpendicular to the longitudinal direction of the line sensor 20 and appear in the image signal S1 at the pitches of the non-aperture portions 19.

In this embodiment, the photoelectric convertor elements 21 of the line sensor 20 and the refractive index profile type lenses 18 of the second SELFOC lens array 16 are arranged at pitches such that the frequency band of the periodic pattern generated due to the pitches of the refractive index profile type lenses 18 are higher than the frequency band of a radiation image information reproduced on the basis of the image signal S1. In this particular embodiment, the pitch S of the refractive index profile type lenses 18 is not larger than double the pitch L of the photoelectric convertor elements 21 of the line sensor 20 ($S \leq 2L$).

It is preferred that the pitch L of the photoelectric convertor elements 21 of the line sensor 20 is in the range of 25 $\mu$m to 250 $\mu$m. The pitch S of the refractive index profile type lenses 18 in the second SELFOC lens array 16 is preferably in the range of 10 $\mu$m to 500 $\mu$m.

Figure 5:
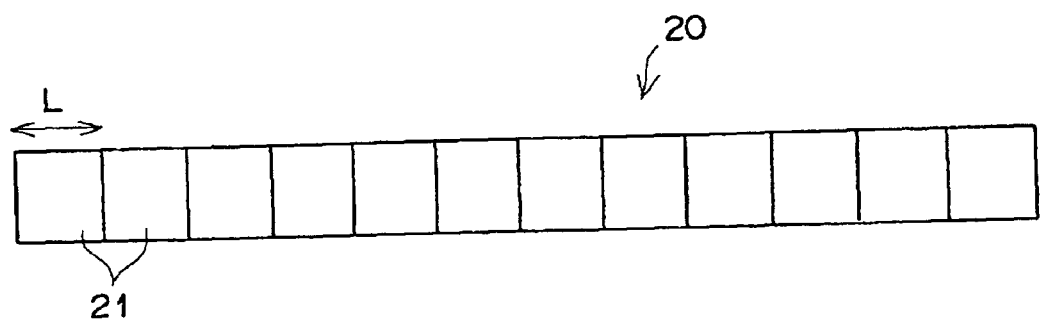
FIG. 5 is a fragmentary cross-sectional view of the line sensor.

The reason why the pitch S of the refractive index profile type lenses 18 is set to be not larger than double the pitch L of the photoelectric convertor elements 21 of the line sensor 20 ($S \leq 2L$) will be described hereinbelow. FIG. 4 is a fragmentary cross-sectional view showing in detail the second SELFOC lens array 16, and FIG. 5 is a fragmentary cross-sectional view of the line sensor 20. The pitch of the refractive index profile type lenses 18 is represented by S ($\mu$m) and the pitch of the photoelectric convertor elements 21 is represented by L ($\mu$m). In the second SELFOC lens array 16, the intensity of transmitted light is reduced at the non-aperture portions 19 and accordingly light impinging upon the SELFOC lens array 16 is modulated into transmitted light having a periodic pattern whose frequency f is 1000/S (cycle/mm). Whereas, the maximum frequency band which the line sensor 20 can detect as an image, that is, the maximum frequency band F of a radiation image which can be reproduced on the basis of the image signal S1, is ½ of 1000/L, that is, F=1000/2L (cycle/mm) from the sampling theorem. Though the maximum frequency band F varies by the kind of the required radiation image, the maximum frequency band F is 3 to 5 cycle/mm in the case of a normal radiation image and 5 to 10 cycle/mm in the case of a radiation image where a high sharpness is required.

Figure 6:
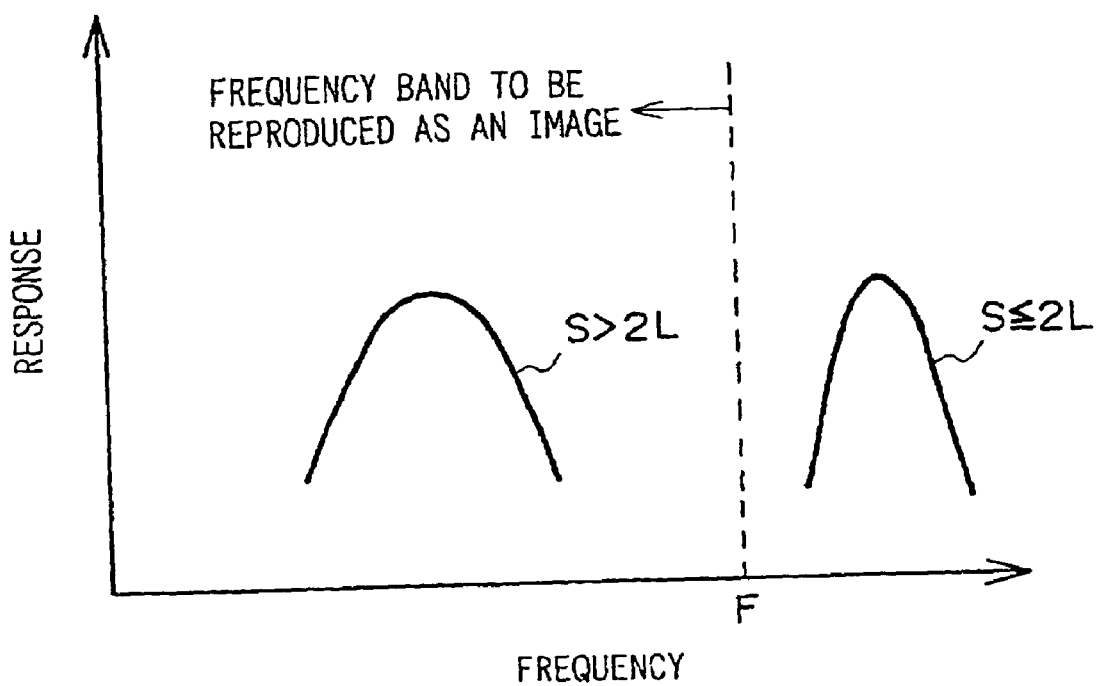
FIG. 6 is a view showing the frequency characteristics of the periodic pattern due to the pitch of the refractive index profile type lenses.

When the frequency f of the periodic pattern of the SELFOC lens array 16 is not lower than the maximum frequency band F of a radiation image which can be reproduced on the basis of the image signal S1, the periodic pattern of the SELFOC lens array 16 cannot affect the radiation image represented by the image signal S1 as can be understood from the frequency characteristics shown in FIG. 6. Conversely, when the frequency f of the periodic pattern of the SELFOC lens array 16 is lower than the maximum frequency band F of a radiation image which can be reproduced on the basis of the image signal S1, the periodic pattern overlaps the spatial frequency of the radiation image and the quality of the image deteriorates. Accordingly, in this particular embodiment, the pitch S of the lenses 18 and the pitch L of the photoelectric convertor elements 21 are set to be $S \leq 2L$ so that $f \geq F$.

When $S \leq 2L$, the periodic pattern is included in the image signal S1 as aliasing noise. Accordingly, it is preferred that a frequency component removal means which removes a frequency component corresponding to the frequency band of the periodic pattern from the image signal S1 be provided.

Figure 8:
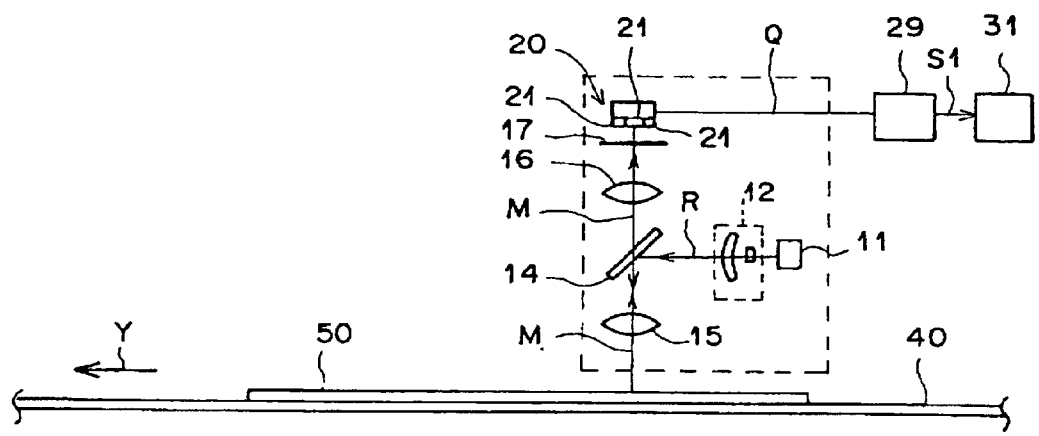
FIG. 8 is a view similar to FIG. 1B but showing another modification of the radiation image read-out apparatus shown in FIG. 1A.

The frequency component removal means may comprise an optical low-pass filter 30 disposed upstream of the line sensor 20 as shown in FIG. 7, or an electric filter 31 which removes aliasing noise from the image signal S1 as shown in FIG. 8. Further, the frequency component removal means may be an analog filter which removes aliasing noise from the image signal before digitized.

Operation of the radiation image read-out apparatus of this embodiment will be described, hereinbelow.

The endless belt 40 is driven to convey the stimulable phosphor sheet 50 stored thereon a radiation image in the direction of arrow Y in FIG. 1A.

While the broad area laser 11 emits a line stimulating light beam R substantially in parallel to the surface of the stimulable phosphor sheet 50. The line stimulating light beam R is converted to a parallel light beam by the optical system 12 (the collimator lens and the toric lens) and reflected by the dichroic mirror 14 to impinge upon the stimulable phosphor sheet 50 in perpendicular thereto after condensed by the first SELFOC lens array 15 into a line beam extending in the direction of arrow X on the surface of the stimulable phosphor sheet 50.

The line stimulating light beam R impinging upon the stimulable phosphor sheet 50 stimulates the stimulable phosphor in the irradiated area and at the same time is scattered inside the stimulable phosphor sheet 50 to stimulate also the stimulable phosphor near the irradiated area. As a result, the stimulated emission M is emitted from the irradiated area and the area adjacent thereto in proportion to the amount of radiation energy stored thereon.

The stimulated emission M is made to a parallel light bundle by the first SELFOC lens array 15, is transmitted through the dichroic mirror 14 and enters the second SELFOC lens array 16. Then the stimulated emission M is converged onto the light receiving faces of photoelectric convertor elements 21 by the second SELFOC lens array 16. At this time, the stimulating light beam R reflected by the surface of the stimulable phosphor sheet 50 is cut by the stimulating light cut filter 17.

The line sensor 20 converts the amount of the stimulated emission M as received by each of the photoelectric convertor elements 21 to an electric signal Q and inputs the electric signal Q into the image signal reading means 29. The image signal reading means 29 digitizes the electric signal Q and stores the digitized electric signal together with the position on the stimulable phosphor sheet 50. Then when the electric signal Q is obtained for the entire area of the stimulable phosphor sheet 50, the image signal reading means 29 outputs an image signal S1 representing the radiation image stored on the stimulable phosphor sheet 50.

As described above, in this embodiment, since the pitch L of the photoelectric convertor elements 21 of the line sensor 20 and the pitch S of the lenses 18 are arranged so that the frequency band of the periodic pattern generated due to the pitch S of the lenses in the refractive index profile type lens array are higher than the frequency band of a radiation image information reproduced on the basis of the image signal S1, unevenness due to the non-aperture portions 19 of the refractive index profile type lens array 16 is not included in the image signal, whereby a sharp image free from stripe-like unevenness due to the non-aperture portions 19 of the refractive index profile type lens array 16 can be obtained.

Further, by removing a frequency component corresponding to the frequency band of the periodic pattern from the image signal S1, a sharper image free from aliasing noise can be obtained.

The radiation image read-out apparatus in accordance with the present invention need not be limited to the radiation image read-out apparatus described above, but may be variously modified. For example, the light source, the condenser optical system between the light source and the stimulable phosphor sheet, the optical system between the sheet and the line sensor, and the line sensor itself maybe other various known structures. Further, the radiation image read-out apparatus may be further provided with an image processing system for carrying out image processing on the image signal S and/or an erasing means which projects erasing light after the image signal is obtained from the stimulable phosphor sheet so that the residual energy of the radiation is fully released from the stimulable phosphor sheet.

Further, though, in the radiation image read-out apparatus of the embodiment described above, the optical system is arranged so that the path of the stimulating light beam R partly overlaps with the path of the stimulated emission M in order to reduce the overall size of the apparatus, the optical system need not be limited to such an arrangement. For example, an optical system in which the path of the stimulating light beam R does not overlap with the path of the stimulated emission M as shown in FIG. 9 may be employed.

Figure 9:
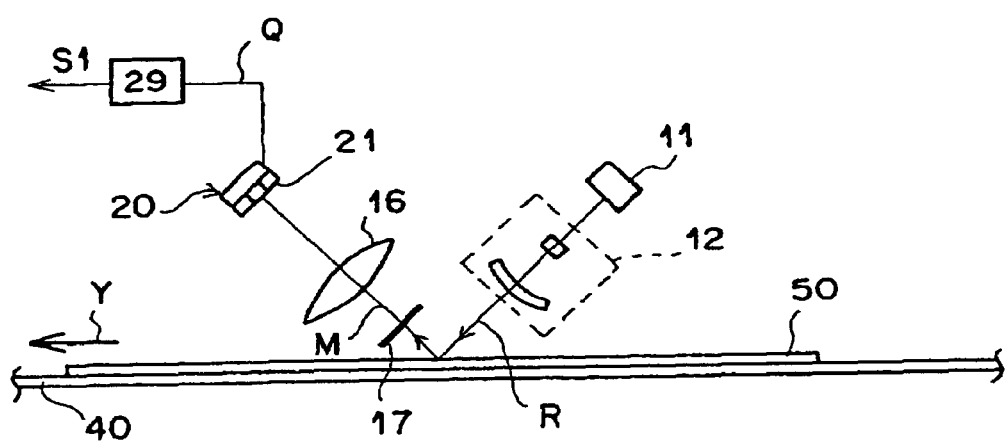
FIG. 9 is a schematic view showing a radiation image read-out apparatus in accordance with another embodiment of the present invention.

That is, the radiation image read-out apparatus in accordance with a second embodiment of the present invention shown in FIG. 9 comprises an endless belt 40 for conveying the stimulable phosphor sheet 50, a broad area laser 11 which emits a line stimulating light beam R at about 45° to the surface of the stimulable phosphor sheet 50, an optical system 12 which is formed by a combination of a collimator lens which condenses the line stimulating light beam R emitted from the broad area laser 11 and a toric lens which spreads the light beam only in one direction, and projects the line stimulating light beam R onto the surface of the stimulable phosphor sheet 50; a SELFOC lens array 16 the optical axis of which is at about 45° to the surface of the stimulable phosphor sheet 50 and about 90° to the direction of travel of the line stimulating light beam R and which converges the stimulated emission M emitted from the stimulable phosphor sheet 50 upon exposure to the stimulating light R onto the light receiving face of a line sensor 20; a stimulating light cut filter 17 which cuts the stimulating light R in the stimulated emission M entering the SELFOC lens array 16; the line sensor 20 which has an array of photoelectric convertor elements 21 which receive the stimulated emission M and convert it into an electric signal Q; and an image signal reading means 29 which reads the signals Q from the respective photoelectric convertor elements 21 and outputs an image signal S1.

Figure 10:
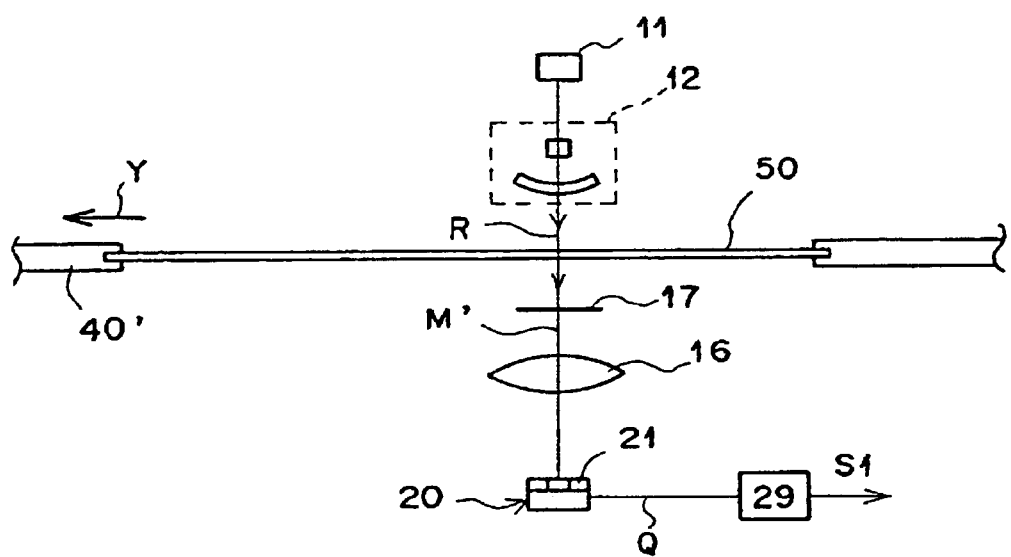
FIG. 10 is a schematic view showing a radiation image read-out apparatus in accordance with still another embodiment of the present invention.

Though, in the first and second embodiments described above, the line stimulating light beam R is projected onto the same surface of the stimulable phosphor sheet 50 as that the line sensor 20 is opposed to, the line stimulating light beam R may be projected onto the surface of the stimulable phosphor sheet 50 opposite to that the line sensor 20 is opposed to as shown in FIG. 10. In the latter case, the support film or the substrate on which the stimulable phosphor layer is formed should be transparent to the stimulated emission M.

The radiation image read-out apparatus in accordance with a third embodiment of the present invention shown in FIG. 10 comprises an endless belt 40' which conveys the stimulable phosphor sheet 50 in the direction of arrow Y holding the leading end portion and the trailing end portion of the stimulable phosphor sheet 50 (no radiation image is recorded in these areas or if any, the radiation image in these areas is generally not important), abroad area laser 11 which emits a line stimulating light beam R substantially in perpendicular to the surface of the stimulable phosphor sheet 50, an optical system 12 which is formed by a combination of a collimator lens which condenses the line stimulating light beam R emitted from the broad area laser 11 and a toric lens which spreads the light beam only in one direction and projects the line stimulating light beam R onto the upper surface of the stimulable phosphor sheet 50; a SELFOC lens array 16 the optical axis of which is at about 90° to the surface of the stimulable phosphor sheet 50 and which converges the stimulated emission M' emitted from the back side of the stimulable phosphor sheet 50 (the side opposite to the side on which the stimulating light beam R impinges) upon exposure to the stimulating light L onto the light receiving face of a line sensor 20; a stimulating light cut filter 17 which cuts the stimulating light L in the stimulated emission M entering the SELFOC lens array 16; the line sensor 20 which has an array of photoelectric convertor elements 21 which receive the stimulated emission M' and convert it into an electric signal; and an image signal reading means 29 which reads the signals Q from the respective photoelectric convertor elements 21 and outputs an image signal S.

What is claimed is:

1. A radiation image read-out apparatus comprising a line stimulating light beam source which projects a line stimulating light beam onto a stimulable phosphor sheet storing thereon radiation image information, a line sensor which comprises a plurality of photoelectric convertor elements arranged in the longitudinal direction of the line irradiated portion to receive stimulated emission emitted from the irradiated portion of the stimulable phosphor sheet or the back side of the sheet opposed to the line irradiated portion and convert the amount of stimulated emission to an electric signal, a light collector means which is disposed between the stimulable phosphor sheet and the line sensor and includes a refractive index profile type lens array which converges the stimulated emission onto the respective photoelectric convertor elements of the line sensor, a scanning means which moves the stimulating light beam source and the line sensor relatively to the stimulable phosphor sheet in a direction different form said longitudinal direction, and an image signal read-out means which reads out the output of the line sensor in sequence in the respective positions in which the stimulating light beam and the line sensor are moved by the scanning means and reads out an image signal representing the radiation image information stored in the stimulable phosphor sheet, wherein the improvement comprises that the photoelectric convertor elements of the line sensor and the refractive index profile type lenses of the refractive index profile type lens array are arranged at pitches such that the frequency band of the periodic pattern generated due to the pitches of the refractive index profile type lenses in said refractive index profile type lens array are higher than the frequency band of a radiation image information reproduced on the basis of the image signal.

2. A radiation image read-out apparatus as defined in claim 1 further comprising a frequency component removal means which removes a frequency component corresponding to the frequency band of the periodic pattern from the image signal.

3. A radiation image read-out apparatus as defined in claim 1 in which the pitch S of the refractive index profile type lenses is not larger than double the pitch L of the photoelectric convertor elements of the line sensor (S≦2L).

4. A radiation image read-out apparatus as defined in claim 3 in which the pitch L of the photoelectric convertor elements of the line sensor is in the range of 25 $\mu$m to 250 $\mu$m.

5. A radiation image read-out apparatus as defined in claim 3 in which the pitch S of the refractive index profile type lenses is in the range of 10 $\mu$m to 500 $\mu$m.

* * * * *